(12) United States Patent
Hassan et al.

(10) Patent No.: US 8,431,752 B2
(45) Date of Patent: *Apr. 30, 2013

(54) METHOD OF MAKING ALKYLENE GLYCOLS

(71) Applicant: H R D Corporation, Houston, TX (US)

(72) Inventors: Abbas Hassan, Sugar Land, TX (US); Aziz Hassan, Sugar Land, TX (US); Rayford G. Anthony, College Station, TX (US); Krishnan Viswanathan, Houston, TX (US); Gregory G. Borsinger, Chatham, NJ (US)

(73) Assignee: H R D Corporation, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/631,828

(22) Filed: Sep. 28, 2012

(65) Prior Publication Data

US 2013/0030223 A1  Jan. 31, 2013

Related U.S. Application Data

(60) Continuation of application No. 12/723,221, filed on Mar. 12, 2010, now Pat. No. 8,304,584, which is a continuation-in-part of application No. 12/335,272, filed on Dec. 15, 2008, now Pat. No. 7,910,069, which is a division of application No. 12/142,443, filed on Jun. 19, 2008, now Pat. No. 7,491,856.

(60) Provisional application No. 60/946,484, filed on Jun. 27, 2007.

(51) Int. Cl.
*C07C 29/10* (2006.01)

(52) U.S. Cl.
USPC ............................................... 568/867

(58) Field of Classification Search .................. None
See application file for complete search history.

(56) References Cited

U.S. PATENT DOCUMENTS

| | | | |
|---|---|---|---|
| 1,743,479 A | 1/1930 | Ramsburg |
| 2,256,999 A | 9/1941 | Castner |
| 2,563,437 A | 8/1951 | Townend et al. |
| 2,664,433 A | 12/1953 | Hudson |
| 2,880,061 A | 3/1959 | Muns et al. |
| 2,918,460 A | 12/1959 | Schappert |
| 2,979,492 A | 4/1961 | Governale et al. |
| 3,000,994 A | 9/1961 | Watson |
| 3,062,801 A | 11/1962 | Hoeg et al. |
| 3,098,108 A | 7/1963 | Aaron |
| 3,166,538 A | 1/1965 | Olson et al. |
| 3,184,221 A | 5/1965 | Mould, Jr. |
| 3,253,053 A | 5/1966 | Bergougnou et al. |
| 3,278,510 A | 10/1966 | Ingberman |
| 3,296,168 A | 1/1967 | Jirik et al. |
| 3,330,818 A | 7/1967 | Derby |
| 3,341,503 A | 9/1967 | Paige et al. |
| 3,522,227 A | 7/1970 | Thomas |
| 3,636,152 A | 1/1972 | Szigeth et al. |
| 3,637,820 A | 1/1972 | Dodman et al. |
| 3,781,320 A | 12/1973 | Irwin |
| 3,807,138 A | 4/1974 | Bellisio |
| 3,853,706 A | 12/1974 | Armbruster |
| 3,869,518 A | 3/1975 | Sze et al. |
| 3,892,798 A | 7/1975 | Heeg et al. |
| 3,912,236 A | 10/1975 | Zipperer et al. |
| 3,928,475 A | 12/1975 | Dassel |
| 3,963,640 A | 6/1976 | Smith |
| 3,984,218 A | 10/1976 | Patel et al. |
| 3,996,012 A | 12/1976 | Zucker |
| 4,017,263 A | 4/1977 | Holmes et al. |
| 4,021,498 A | 5/1977 | Alexanderson et al. |
| 4,075,082 A | 2/1978 | Doelp et al. |
| 4,075,258 A | 2/1978 | Caulk et al. |
| 4,083,944 A | 4/1978 | Chalmers |
| 4,155,899 A | 5/1979 | Lemper et al. |
| 4,169,870 A | 10/1979 | Takahashi |
| 4,179,375 A | 12/1979 | Smith |
| 4,184,924 A | 1/1980 | Hornbaker et al. |
| 4,238,415 A | 12/1980 | Bryan |
| 4,275,034 A | 6/1981 | Friedman et al. |
| 4,277,632 A | 7/1981 | Kumazawa et al. |
| 4,355,142 A | 10/1982 | Khungar et al. |
| 4,425,232 A | 1/1984 | Lawrence et al. |
| 4,508,537 A | 4/1985 | Fenton et al. |
| 4,517,022 A | 5/1985 | Harvey |
| 4,544,489 A | 10/1985 | Campbell et al. |
| 4,560,813 A | 12/1985 | Collier et al. |
| 4,564,715 A | 1/1986 | Briggs et al. |
| 4,571,437 A | 2/1986 | Caskey et al. |
| 4,571,440 A | 2/1986 | Keen et al. |
| 4,579,982 A | 4/1986 | Briggs et al. |
| 4,649,032 A | 3/1987 | Snavely, Jr. et al. |
| 4,701,571 A | 10/1987 | Soo et al. |
| 4,724,269 A | 2/1988 | Suzuki et al. |
| 4,740,621 A | 4/1988 | Adams et al. |
| 4,772,757 A | 9/1988 | Lailach et al. |

(Continued)

FOREIGN PATENT DOCUMENTS

| | | |
|---|---|---|
| EP | 1604969 | 12/2005 |
| JP | 61183235 | 8/1986 |

(Continued)

OTHER PUBLICATIONS

Office Action dated Apr. 20, 2010 for U.S. Appl. No. 12/427,286.

(Continued)

Primary Examiner — Brian J Davis

(74) Attorney, Agent, or Firm — Porter Hedges LLP; Timothy S. Westby

(57) ABSTRACT

Herein disclosed is a method of hydrating an alkylene oxide that includes introducing an alkylene oxide into water to form a first stream; flowing the first stream through a high shear device to produce a second stream; and contacting the second stream with a catalyst in a reactor to hydrate the alkylene oxide and form an alkylene glycol.

17 Claims, 2 Drawing Sheets

U.S. PATENT DOCUMENTS

| | | | |
|---|---|---|---|
| 4,800,017 A | 1/1989 | Krishnaswamy et al. |
| 4,886,905 A | 12/1989 | Larkins, Jr. |
| 4,914,029 A | 4/1990 | Caransa et al. |
| 4,950,831 A | 8/1990 | Staton et al. |
| 4,959,183 A | 9/1990 | Jameson |
| 4,973,770 A | 11/1990 | Evans |
| 5,008,462 A | 4/1991 | Ishizuka et al. |
| 5,009,816 A | 4/1991 | Weise et al. |
| 5,081,303 A | 1/1992 | Greenfield et al. |
| 5,102,635 A | 4/1992 | Delaney et al. |
| 5,104,674 A | 4/1992 | Chen et al. |
| 5,107,048 A | 4/1992 | Huss, Jr. et al. |
| 5,140,674 A | 8/1992 | Anderson et al. |
| 5,146,011 A | 9/1992 | Shen et al. |
| 5,157,158 A | 10/1992 | Berna et al. |
| 5,160,714 A | 11/1992 | Hardison |
| 5,194,145 A | 3/1993 | Schoendorfer |
| 5,205,926 A | 4/1993 | Lawrence |
| 5,264,087 A | 11/1993 | Lowery et al. |
| 5,313,009 A | 5/1994 | Guenkel et al. |
| 5,382,358 A | 1/1995 | Yeh |
| 5,451,348 A | 9/1995 | Kingsley |
| 5,498,766 A | 3/1996 | Stuart et al. |
| 5,506,363 A | 4/1996 | Grate et al. |
| 5,511,382 A | 4/1996 | Denis et al. |
| 5,522,553 A | 6/1996 | LeClair et al. |
| 5,531,425 A | 7/1996 | Skibo et al. |
| 5,538,191 A | 7/1996 | Holl |
| 5,608,017 A | 3/1997 | Kamiyama et al. |
| 5,616,806 A | 4/1997 | Nagata et al. |
| 5,616,807 A | 4/1997 | Foster et al. |
| 5,622,650 A | 4/1997 | Rourke |
| 5,648,054 A | 7/1997 | DeBerry |
| 5,679,870 A | 10/1997 | Tustin et al. |
| 5,696,305 A | 12/1997 | Klingler et al. |
| 5,710,342 A | 1/1998 | Imre et al. |
| 5,710,355 A | 1/1998 | Krishnamurti |
| 5,730,784 A | 3/1998 | Smith et al. |
| 5,733,516 A | 3/1998 | DeBerry |
| 5,756,714 A | 5/1998 | Antrim et al. |
| 5,763,691 A | 6/1998 | Kawabe et al. |
| 5,763,697 A | 6/1998 | Hermann et al. |
| 5,777,189 A | 7/1998 | Alexanyan et al. |
| 5,877,350 A | 3/1999 | Langer et al. |
| 5,972,661 A | 10/1999 | Kubera et al. |
| 6,000,840 A | 12/1999 | Paterson |
| 6,092,359 A | 7/2000 | Ackermann et al. |
| 6,137,014 A | 10/2000 | Godfried Andre Van Kruchten |
| 6,187,825 B1 | 2/2001 | Guntherberg et al. |
| 6,187,972 B1 | 2/2001 | Kawabe et al. |
| 6,194,625 B1 | 2/2001 | Graves et al. |
| 6,241,472 B1 | 6/2001 | Bosch et al. |
| 6,251,289 B1 | 6/2001 | Sherman |
| 6,315,964 B1 | 11/2001 | Knifton et al. |
| 6,331,314 B1 | 12/2001 | Klinksiek et al. |
| 6,368,366 B1 | 4/2002 | Langer et al. |
| 6,368,367 B1 | 4/2002 | Langer et al. |
| 6,383,237 B1 | 5/2002 | Langer et al. |
| 6,521,181 B2 | 2/2003 | Lee et al. |
| 6,530,964 B2 | 3/2003 | Langer et al. |
| 6,544,492 B1 | 4/2003 | DeBerry |
| 6,568,900 B2 | 5/2003 | Conrad et al. |
| 6,576,802 B2 | 6/2003 | Knifton et al. |
| 6,596,253 B1 | 7/2003 | Barrere-Tricca et al. |
| 6,670,406 B2 | 12/2003 | Hofmann et al. |
| 6,693,213 B1 | 2/2004 | Kolena et al. |
| 6,742,774 B2 | 6/2004 | Holl |
| 6,752,529 B2 | 6/2004 | Holl |
| 6,765,110 B2 | 7/2004 | Warner et al. |
| 6,768,021 B2 | 7/2004 | Horan et al. |
| 6,787,036 B2 | 9/2004 | Long |
| 6,809,217 B1 | 10/2004 | Colley et al. |
| 6,822,007 B2 | 11/2004 | Ketley et al. |
| 6,866,411 B1 | 3/2005 | Stelzer et al. |
| 6,916,963 B2 | 7/2005 | van Hal et al. |
| 7,001,502 B1 | 2/2006 | Satchwell et al. |
| 7,037,433 B2 | 5/2006 | Abu-Orf et al. |
| 7,074,978 B2 | 7/2006 | Pohl |
| 7,105,092 B2 | 9/2006 | Chiba |
| 7,165,881 B2 | 1/2007 | Holl |
| 7,276,126 B2 | 10/2007 | Nehmer et al. |
| 7,297,651 B2 | 11/2007 | Khattaty et al. |
| 7,319,180 B2 | 1/2008 | Smith, Jr. et al. |
| 7,383,723 B2 | 6/2008 | Tregub et al. |
| 7,419,652 B2 | 9/2008 | Khattaty et al. |
| 7,425,269 B2 | 9/2008 | Hoage |
| 7,427,383 B2 | 9/2008 | Cisneros |
| 7,461,970 B2 | 12/2008 | Brown |
| 7,473,348 B2 | 1/2009 | Koch |
| 7,473,811 B2 | 1/2009 | Eilos et al. |
| 7,479,576 B1 | 1/2009 | Hassan et al. |
| 7,491,856 B2 | 2/2009 | Hassan et al. |
| 7,524,467 B2 | 4/2009 | Pohl |
| 7,538,237 B2 | 5/2009 | Holl |
| 7,556,679 B2 | 7/2009 | Lee et al. |
| 7,575,728 B2 | 8/2009 | Holl et al. |
| 7,662,288 B2 | 2/2010 | Yamasaki et al. |
| 7,842,184 B2 | 11/2010 | Hassan et al. |
| 7,884,250 B2 | 2/2011 | Hassan et al. |
| 7,910,069 B2 | 3/2011 | Hassan et al. |
| 7,919,534 B2 | 4/2011 | Wood et al. |
| 7,922,900 B2 | 4/2011 | Hassan et al. |
| 7,942,572 B2 | 5/2011 | Arletti et al. |
| 8,022,153 B2 | 9/2011 | Hassan et al. |
| 8,071,046 B2 | 12/2011 | Hassan et al. |
| 8,080,684 B2 | 12/2011 | Hassan et al. |
| 8,133,447 B2 | 3/2012 | Hassan et al. |
| 8,147,768 B2 | 4/2012 | Hassan et al. |
| 8,153,076 B2 | 4/2012 | Hassan et al. |
| 8,212,086 B2 * | 7/2012 | Hassan et al. ............ 568/867 |
| 2001/0020344 A1 | 9/2001 | Thompson et al. |
| 2002/0010249 A1 | 1/2002 | Bilimoria |
| 2002/0120017 A1 | 8/2002 | Bohn et al. |
| 2005/0150155 A1 | 7/2005 | Waldron et al. |
| 2005/0255397 A1 | 11/2005 | Yamamoto et al. |
| 2005/0272945 A1 | 12/2005 | Larke |
| 2006/0041166 A1 | 2/2006 | Stuart |
| 2006/0054205 A1 | 3/2006 | Yabe et al. |
| 2006/0141107 A1 | 6/2006 | Schwimmer et al. |
| 2007/0294935 A1 | 12/2007 | Waldron et al. |
| 2008/0116116 A1 | 5/2008 | Koch |
| 2008/0144431 A1 | 6/2008 | Troxler |
| 2008/0319320 A1 | 12/2008 | Ottoboni et al. |
| 2009/0005552 A1 | 1/2009 | Hassan et al. |
| 2009/0005553 A1 | 1/2009 | Hassan et al. |
| 2009/0005619 A1 | 1/2009 | Hassan et al. |
| 2009/0005622 A1 | 1/2009 | Hassan et al. |
| 2009/0018367 A1 | 1/2009 | Wyatt |
| 2009/0136392 A1 | 5/2009 | Hassan et al. |
| 2009/0136393 A1 | 5/2009 | Hassan et al. |
| 2009/0136395 A1 | 5/2009 | Hassan et al. |
| 2009/0136396 A1 | 5/2009 | Hassan et al. |
| 2009/0180940 A1 | 7/2009 | Hassan et al. |
| 2009/0306419 A1 | 12/2009 | Myong et al. |
| 2009/0323458 A1 | 12/2009 | Fischer et al. |
| 2010/0004419 A1 | 1/2010 | Hassan et al. |
| 2010/0183486 A1 | 7/2010 | Hassan et al. |
| 2010/0222615 A1 | 9/2010 | Hassan et al. |
| 2012/0226078 A1 * | 9/2012 | Hassan et al. ............ 568/867 |

FOREIGN PATENT DOCUMENTS

| | | |
|---|---|---|
| JP | 2000143706 | 5/2000 |
| JP | 2002003505 | 1/2002 |
| JP | 2002121353 | 4/2002 |
| JP | 2007505201 | 3/2007 |
| WO | 9843725 | 10/1998 |
| WO | 02064708 A2 | 8/2002 |
| WO | 2005039745 | 5/2005 |
| WO | 2005108533 | 11/2005 |
| WO | 2006079562 | 8/2006 |
| WO | 2007023864 | 3/2007 |

OTHER PUBLICATIONS

Office Action dated Apr. 20, 2010 for U.S. Appl. No. 12/411,660.

Office Action dated Apr. 23, 2010 for U.S. Appl. No. 12/568,155.

Office Action dated Apr. 27, 2010 for U.S. Appl. No. 12/568,280.

Office Action dated May 5, 2010 for U.S. Appl. No. 12/142,120.
IKA-Rotor-Stator Generators—2003 Processing Ctalog (38 pgs.).
Gogate, et al. "Cavitation: A technology on the horizon," Current Science 91, No. 1, Jul. 2006, pp. 35-46 (12 pgs.).
Office Action dated Jun. 25, 2009 for U.S. Appl. No. 12/142,447.
Office Action dated Jan. 7, 2010 for U.S. Appl. No. 12/142,447.
Office Action dated May 13, 2010 for U.S. Appl. No. 12/142,447.
Office Action dated Feb. 4, 2010 for U.S. Appl. No. 12/492,721.
Office Action dated Feb. 18, 2010 for U.S. Appl. No. 12/635,433.
Office Action dated Feb. 18, 2010 for U.S. Appl. No. 12/635,454.
Office Action dated May 14, 2010 for U.S. Appl. No. 12/137,441.
Office Action dated Feb. 19, 2010 for U.S. Appl. No. 12/144,459.
Office Action dated Sep. 2, 2009 for U.S. Appl. No. 12/142,433.
Office Action dated Jan. 29, 2010 for U.S. Appl. No. 12/142,433.
Office Action dated May 24, 2011 for U.S. Appl. No. 12/142,433.
Office Action dated Apr. 30, 2010 for U.S. Appl. No. 12/141,191.
Office Action dated Oct. 27, 2009 for U.S. Appl. No. 12/142,120.
Office Action dated May 5, 2010 for U.S. Appl. No. 12/571,537.
Office Action dated Feb. 24, 2011 for U.S. Appl. No. 12/796,358.
Office Action dated Feb. 29, 2012 for U.S. Appl. No. 12/146,733.
Office Action dated Jun. 3, 2011 for U.S. Appl. No. 12/568,155.
Office Action dated Jun. 2, 2011 for U.S. Appl. No. 12/427,286.
Office Action dated Jun. 3, 2011 for U.S. Appl. No. 12/568,280.
Office Action dated Nov. 15, 2011 for U.S. Appl. No. 13/028,100.
Office Action dated Jul. 28, 2010 for U.S. Appl. No. 12/635,433.
Office Action dated Jun. 28, 2010 for U.S. Appl. No. 12/335,272.
Chinese Office Action dated May 22, 2012 Issued in corresponding Application No. 200880021253.X (7 pgs.).
Canadian Office Action dated Aug. 31, 2011 Issued in corresponding Application No. 2,687,638 (2 pgs.).
Canadian Office Action dated Apr. 24, 2012 Issued in corresponding Application No. 2,687,638 (4 pgs.).
Eurasian Office Action dated Feb. 1, 2012 Issued in corresponding Application No. 200901501/13 (2 pgs.).
Search Report and Written Opinion for International Application No. PCT/US2008/068219 dated Jan. 7, 2009 (7 pgs.).
Search Report and Written Opinion for International Application No. PCT/US2011/026719 dated Jun. 16, 2011 (9 pgs.).
Search Report and Written Opinion for International Application No. PCT/US2008/068161 dated Sep. 24, 2008 (6 pgs.).
Written Opinion for International Application No. PCT/US2008/066572 dated Aug. 28, 2008 (3 pgs.).
Search Report for International Application No. PCT/US2008/066572 dated Aug. 28, 2008 (3 pgs.).
Roto-Stator Generators for Batch, In-Line Mixing by IKA, dated Apr. 14, 2010 (5 pgs.).
Green, D.W. "Chemical Reactors", Perry's Chemical Engineers' Handbook, 7th Edition, Section 23, pp. 50-52 (1997) (5 pgs.).
Lopes-Filho, et al. "Intermittent Milling and Dynamic Steeping Process for Corn Starch Recovery", CCHEM, Cereal Chemistry Abstract, vol. 74, No. 5, Sep./Oct. 1997 (2 pgs.).
Wiley & Sons, Inc., "Mixing and Blending," Kirk-Othmer Encyclopedia of Chemical Technology, dated Apr. 16, 2010, pp. 1-71 (71 pgs.).
Notice of Allowance dated Dec. 4, 2012 for corresponding U.S. Appl. No. 13/472,298 (22 pgs.).

* cited by examiner

METHOD OF MAKING ALKYLENE GLYCOLS

CROSS-REFERENCE TO RELATED APPLICATIONS

This application is a continuation of U.S. patent application Ser. No. 12/723,221, filed Mar. 12, 2010 (now U.S. Pat. No. 8,304,584, issued Nov. 6, 2012). This application is a continuation-in-part of U.S. patent application Ser. No. 12/335,272, filed Dec. 15, 2008 (now U.S. Pat. No. 7,910,069, issued Mar. 22, 2011), which is a divisional application of U.S. patent application Ser. No. 12/142,443, filed Jun. 19, 2008 (now U.S. Pat. No. 7,491,856, issued Feb. 17, 2009), which claims the benefit under 35 U.S.C. §119(e) of U.S. Provisional Patent Application No. 60/946,484, filed Jun. 27, 2007. The disclosure of each of the aforementioned applications is hereby incorporated herein by reference.

STATEMENT REGARDING FEDERALLY SPONSORED RESEARCH OR DEVELOPMENT

Not Applicable.

BACKGROUND

1. Field of the Invention

This invention relates generally to the field of chemical reactions. More specifically, the invention relates to methods of making alkylene glycols incorporating high shear mixing.

2. Background of the Invention

Ethylene glycol is used as antifreeze in cooling and heating systems, in hydraulic brake fluids, as an industrial humectant, as an ingredient of electrolytic condensers, as a solvent in the paint and plastics industries, in the formulations of printers' inks, stamp pad inks, and inks for ballpoint pens, as a softening agent for cellophane, and in the synthesis of safety explosives, plasticizers, synthetic fibers (TERYLENE®, DACRON®), and synthetic waxes. Ethylene glycol is also used to de-ice airport runways and aircraft. Plainly, ethylene glycol is an industrially important compound with many applications.

Prior methods for hydrating alkylene oxides to the alkylene glycols include the direct hydration reaction without benefit of catalyst and the catalytic hydration of alkylene oxides using mineral acid catalysts. These mineral acid catalytic reactions are homogeneous thereby posing a problem for the commercial production of glycols since the catalyst is carried over into the product and must be separated. Present commercial processes use a noncatalytic hydration procedure which must use large ratios of water to alkylene oxide thereby presenting a problem of separation of the water from the finished product. This separation consumes large amounts of energy which recently has been the cause of much concern.

Recently, attempts have been made to discover a new catalyst for the hydration of alkylene oxides to the respective glycols. For example, other catalytic processes use tetramethyl ammonium iodide and tetraethyl ammonium bromide, or organic tertiary amines such as triethylamine and pyrridine. Despite a focus on the catalyst technology, little has been done toward improving the mixing of the alkylene oxide with the water phase to optimize the reaction.

Consequently, there is a need for accelerated methods for making alkyl glycols by improving the mixing of ethylene oxide into the water phase.

SUMMARY

Herein disclosed is a method of hydrating an alkylene oxide. In an embodiment, the method comprises (a) introducing an alkylene oxide into water to form a first stream; (b) flowing the first stream through a high shear device to produce a second stream; and (c) contacting the second stream with a catalyst in a reactor to hydrate the alkylene oxide and form an alkylene glycol. In some embodiments, alkylene oxide comprises ethylene oxide, propylene oxide, butylene oxide, or combinations thereof. In some embodiments, step (b) of the method comprises subjecting the first stream to high shear mixing at a tip speed of at least about 23 m/sec. In some embodiments, step (b) of the method comprises subjecting the first stream to a shear rate of greater than about 20,000 s$^{-1}$. In some embodiments, producing the second stream comprises an energy expenditure of at least about 1000 W/m$^3$. In some embodiments, the catalyst comprises an amine, an acid catalyst, an organometallic compound, an alkali metal halide, a quaternary ammonium halide, zeolites, or combinations thereof. In some embodiments, the alkylene glycol comprises ethylene glycol.

Also disclosed herein is a method of hydrating an alkylene oxide. The method comprises (a) introducing an alkylene oxide into water to form a first stream; (b) passing the first stream through a high shear device to hydrate the alkylene oxide to produce a second stream comprising an alkylene glycol; and (c) recovering the alkylene glycol from the second stream. In some embodiments, the high shear device comprises a catalytic surface.

A method of producing polyethylene glycol is described in this disclosure. The method comprises introducing ethylene oxide and water or ethylene glycol or ethylene glycol oligomer into a high shear device to produce a first stream; and subjecting the first stream to a catalyst that promotes the formation of polyethylene glycol. In some embodiments, the high shear device comprises a catalytic surface that promotes the formation of polyethylene glycol.

Furthermore, a system for hydrating an alkylene oxide is disclosed. The system comprises at least one high shear device configured to form a mixed stream of an alkylene oxide and water comprising a rotor and a stator, the rotor and the stator are separated by a shear gap in the range of from about 0.02 mm to about 5 mm, wherein the shear gap is a minimum distance between the rotor and the stator, and wherein the high shear device is capable of producing a tip speed of the at least one rotor of greater than about 23 m/s (4,500 ft/min); a pump configured for delivering a liquid stream to the high shear device; and a reactor for hydrating the alkylene oxide coupled to the high shear device, the reactor is configured for receiving the mixed stream from the high shear device. In some embodiments, the high shear device comprises two or more rotors and two or more stators. In some embodiments, the high shear device comprises a rotor tip and the device is configured for operating at a flow rate of at least 300 L/h at a tip speed of at least about 23 m/sec. In some embodiments, the high shear device is configured to provide an energy expenditure greater than about 1000 W/m$^3$. In some embodiments, the system further comprises more than one high shear device. In some embodiments, the high shear device has a tip speed of greater than about 20 m/s (4000 ft/min). In some embodiments, the system further comprises a fixed bed reactor, the reactor comprising a hydration catalyst. In some embodiments, the high shear device comprises at least two generators. In some embodiments, the high shear device comprises a catalytic surface.

Furthermore, embodiments disclosed herein pertain to a method of hydrating an alkylene oxide that may include introducing an alkylene oxide into water to form a first stream; flowing the first stream through a high shear device to produce a second stream; and contacting the second stream with a catalyst in a reactor to hydrate the alkylene oxide and form an alkylene glycol. The method may include operating the high shear device at a tip speed of at least about 23 m/sec. the method may include operating the high shear device at a shear rate of greater than about 20,000 s$^{-1}$.

The alkylene oxide may be, for example, ethylene oxide, propylene oxide, butylene oxide, or combinations thereof. Producing the second stream may entail an energy expenditure of at least about 1000 W/m$^3$. The catalyst may include an amine, an acid catalyst, an organometallic compound, an alkali metal halide, a quaternary ammonium halide, zeolites, or combinations thereof. The alkylene glycol comprises may include glycol.

Further embodiments of the disclosure pertain to a method of hydrating an alkylene oxide that may include introducing an alkylene oxide into water to form a first stream; flowing the first stream through a high shear device to produce a second stream; and contacting the second stream with a catalyst in a reactor. The method may also include recovering the alkylene glycol from the second stream. The method may also include operating the high shear device at a shear rate in the range of about 20,000 s$^{-1}$ to about 1,600,000 s$^{-1}$.

In aspects, in the reactor the alkylene oxide may be hydrated to form an alkylene glycol. The high shear device may include a catalytic surface. In other aspects, in the reactor the alkyline oxide may be hydrated to form ethylene glycol. The reactor may be a fixed bed reactor. The catalyst may be a hydration catalyst.

Other embodiments disclosed herein pertain to a method of producing polyethylene glycol that may include introducing a first component comprising ethylene oxide and a second component selected from the group consisting of water, ethylene glycol, and ethylene glycol oligomer, into a high shear device to produce a first stream; and reacting at least a portion of the first stream with a catalyst to produce polyethylene glycol. The method may further include operating the high shear device at a shear rate in the range of about 20,000 s$^{-1}$ to about 1,600,000 s$^{-1}$.

In aspects reacting step may occur in a fixed bed reactor. In other aspects, the high shear device may include a catalytic surface. In yet other aspects, the high shear device may include a catalytic surface that promotes formation of additional polyethylene glycol.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

NOTATION AND NOMENCLATURE

Figure 1:
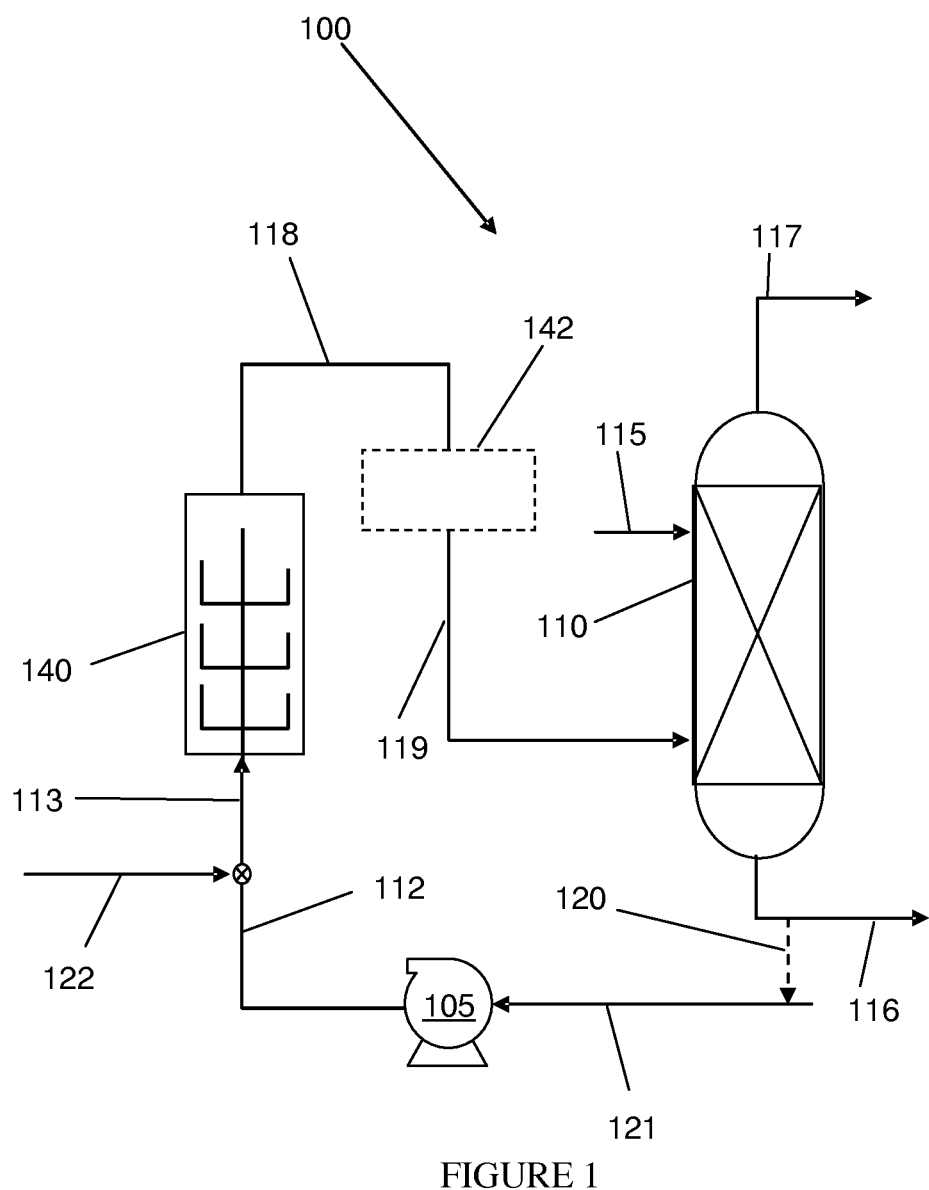
FIG. 1 is a process flow diagram of a process for the hydration of an alkylene oxide with water in liquid phase, according to certain embodiments of the invention.

The term "catalytic surface" is used herein to refer to a surface in a device that is constructed with catalytic material (such as metals, alloys, etc.) so that catalytic activity is manifested when suitable substance comes in touch with said catalytic surface. The use of the term "catalytic surface" in this document includes all such surfaces regardless of the shape and size of surface, material of construct, method of make, degree of activity, or purpose of use.

Certain terms are used throughout the following description and claims to refer to particular system components. This document does not intend to distinguish between components that differ in name but not function. In the following discussion and in the claims, the terms "including" and "comprising" are used in an open-ended fashion, and thus should be interpreted to mean "including, but not limited to . . . ".

DETAILED DESCRIPTION OF THE PREFERRED EMBODIMENTS

Methods and systems for preparing alkylene glycols are described herein. The methods and systems incorporate the novel use of a high shear device to promote dispersion and solubility of an alkylene oxide in water. The high shear device may allow for lower reaction temperatures and pressures and may also reduce reaction time. Further advantages and aspects of the disclosed methods and system are described below.

In an embodiment, a method of making an alkylene glycol comprises introducing an alkylene oxide gas into a liquid water stream to form a gas-liquid stream. The method further comprises flowing the gas-liquid stream through a high shear device so as to form a dispersion with gas bubbles having a mean diameter less than about 1 micron. In addition the method comprises contacting the gas-liquid stream with a catalyst in a reactor to hydrate the alkylene oxide and form the alkylene glycol.

In an embodiment, a system for making an alkylene glycol comprises at least one high shear device configured to form a dispersion of an alkylene oxide and water. The high shear device comprises a rotor and a stator. The rotor and the stator are separated by a shear gap in the range of from about 0.02 mm to about 5 mm. The shear gap is a minimum distance between the rotor and the stator. The high shear device is capable of producing a tip speed of the at least one rotor of greater than about 23 m/s (4,500 ft/min). In addition, the system comprises a pump configured for delivering a liquid stream comprising liquid phase to the high shear device. The system also comprises a reactor for hydrating the alkylene oxide coupled to said high shear device. The reactor is configured for receiving the dispersion from the high shear device.

The disclosed methods and systems for the hydration of alkylene oxides employ a high shear mechanical device to provide rapid contact and mixing of the alkylene oxide gas and water in a controlled environment in the reactor/mixer device. The term "alkylene oxide gas" as used herein includes both substantially pure alkylene oxides as well as gaseous mixtures containing alkylene oxides. In particular, embodiments of the systems and methods may be used in the production of alkylene glycols from the hydration of alkylene oxides. Preferably, the method comprises a heterogeneous phase reaction of liquid water with an alkylene oxide gas. The high shear device reduces the mass transfer limitations on the reaction and thus increases the overall reaction rate. Furthermore, in some embodiments, liquid alkylene oxides are introduced into the high shear mechanical device to be intimately mixed with water for the hydration reactions of alkylene oxides.

Chemical reactions involving liquids, gases and solids rely on time, temperature, and pressure to define the rate of reactions. In cases where it is desirable to react two or more raw materials of different phases (e.g. solid and liquid; liquid and gas; solid, liquid and gas), one of the limiting factors in controlling the rate of reaction involves the contact time of the reactants. In the case of heterogeneously catalyzed reactions there is the additional rate limiting factor of having the reacted products removed from the surface of the catalyst to enable the catalyst to catalyze further reactants. Contact time for the reactants and/or catalyst is often controlled by mixing which provides contact with two or more reactants involved in a chemical reaction. A reactor assembly that comprises an external high shear device or mixer as described herein makes possible decreased mass transfer limitations and thereby allows the reaction to more closely approach kinetic limitations. When reaction rates are accelerated, residence times may be decreased, thereby increasing obtainable throughput. Product yield may be increased as a result of the high shear system and process. Alternatively, if the product yield of an existing process is acceptable, decreasing the required residence time by incorporation of suitable high shear may allow for the use of lower temperatures and/or pressures than conventional processes.

System for Hydration Alkylene Oxides

A high shear alkylene oxide hydration system will now be described in relation to FIG. 1, which is a process flow diagram of an embodiment of a high shear system 100 for the production of alkylene glycols via the hydration of alkylene oxides. The basic components of a representative system include external high shear device (HSD) 140, vessel 110, and pump 105. As shown in FIG. 1, the high shear device may be located external to vessel/reactor 110. Each of these components is further described in more detail below. Line 121 is connected to pump 105 for introducing either an alkylene oxide reactant. Line 113 connects pump 105 to HSD 140, and line 118 connects HSD 140 to vessel 110. Line 122 is connected to line 113 for introducing an alkylene oxide gas. Line 117 is connected to vessel 110 for removal of unreacted alkylene oxides, and other reaction gases. Additional components or process steps may be incorporated between vessel 110 and HSD 140, or ahead of pump 105 or HSD 140, if desired. High shear devices (HSD) such as a high shear, or high shear mill, are generally divided into classes based upon their ability to mix fluids. Mixing is the process of reducing the size of inhomogeneous species or particles within the fluid. One metric for the degree or thoroughness of mixing is the energy density per unit volume that the mixing device generates to disrupt the fluid particles. The classes are distinguished based on delivered energy density. There are three classes of industrial mixers having sufficient energy density to consistently produce mixtures or emulsions with particle or bubble sizes in the range of 0 to 50 microns. High shear mechanical devices include homogenizers as well as colloid mills.

High shear devices (HSD) such as a high shear, or high shear mill, are generally divided into classes based upon their ability to mix fluids. Mixing is the process of reducing the size of inhomogeneous species or particles within the fluid. One metric for the degree or thoroughness of mixing is the energy density per unit volume that the mixing device generates to disrupt the fluid particles. The classes are distinguished based on delivered energy density. There are three classes of industrial mixers having sufficient energy density to consistently produce mixtures or emulsions with particle or bubble sizes in the range of 0 to 50 µm.

Homogenization valve systems are typically classified as high energy devices. Fluid to be processed is pumped under very high pressure through a narrow-gap valve into a lower pressure environment. The pressure gradients across the valve and the resulting turbulence and cavitations act to break-up any particles in the fluid. These valve systems are most commonly used in milk homogenization and can yield average particle size range from about 0.01 µm to about 1 µm. At the other end of the spectrum are high shear systems classified as low energy devices. These systems usually have paddles or fluid rotors that turn at high speed in a reservoir of fluid to be processed, which in many of the more common applications is a food product. These systems are usually used when average particle, or bubble, sizes of greater than 20 microns are acceptable in the processed fluid.

Between low energy—high shears and homogenization valve systems, in terms of the mixing energy density delivered to the fluid, are colloid mills, which are classified as intermediate energy devices. The typical colloid mill configuration includes a conical or disk rotor that is separated from a complementary, liquid-cooled stator by a closely-controlled rotor-stator gap, which is maybe between 0.025 mm and 10.0 mm. Rotors are usually driven by an electric motor through a direct drive or belt mechanism. Many colloid mills, with proper adjustment, can achieve average particle, or bubble, sizes of about 0.01 µm to about 25 µm in the processed fluid. These capabilities render colloid mills appropriate for a variety of applications including colloid and oil/water-based emulsion processing such as that required for cosmetics, mayonnaise, silicone/silver amalgam formation, or roofing-tar mixing.

An approximation of energy input into the fluid (kW/L/min) can be made by measuring the motor energy (kW) and fluid output (L/min). In embodiments, the energy expenditure of a high shear device is greater than 1000 W/m$^3$. In embodiments, the energy expenditure is in the range of from about 3000 W/m$^3$ to about 7500 W/m$^3$. The shear rate generated in a high shear device may be greater than 20,000 s$^{-1}$. In embodiments, the shear rate generated is in the range of from 20,000 s$^{-1}$ to 100,000 s$^{-1}$.

Tip speed is the velocity (m/sec) associated with the end of one or more revolving elements that is transmitting energy to the reactants. Tip speed, for a rotating element, is the circumferential distance traveled by the tip of the rotor per unit of time, and is generally defined by the equation V (m/sec) $=\pi \cdot D \cdot n$, where V is the tip speed, D is the diameter of the rotor, in meters, and n is the rotational speed of the rotor, in revolutions per second. Tip speed is thus a function of the rotor diameter and the rotation rate. Also, tip speed may be calculated by multiplying the circumferential distance transcribed by the rotor tip, $2\pi R$, where R is the radius of the rotor (meters, for example) times the frequency of revolution (for example revolutions (meters, for example) times the frequency of revolution (for example revolutions per minute, rpm).

For colloid mills, typical tip speeds are in excess of 23 m/sec (4500 ft/min) and can exceed 40 m/sec (7900 ft/min). For the purpose of the present disclosure the term 'high shear' refers to mechanical rotor-stator devices, such as mills or mixers, that are capable of tip speeds in excess of 5 m/sec (1000 ft/min) and require an external mechanically driven power device to drive energy into the stream of products to be reacted. A high shear device combines high tip speeds with a very small shear gap to produce significant friction on the material being processed. Accordingly, a local pressure in the range of about 1000 MPa (about 145,000 psi) to about 1050 MPa (152,300 psi) and elevated temperatures at the tip of the shear mixer are produced during operation. In certain embodiments, the local pressure is at least about 1034 MPa (about 150,000 psi).

Referring now to FIG. 1, there is presented a schematic diagram of a high shear device 200. High shear device 200 comprises at least one rotor-stator combination. The rotor-stator combinations may also be known as generators 220, 230, 240 or stages without limitation. The high shear device 200 comprises at least two generators, and most preferably, the high shear device comprises at least three generators.

The first generator 220 comprises rotor 222 and stator 227. The second generator 230 comprises rotor 223, and stator 228; the third generator comprises rotor 224 and stator 229. For each generator 220, 230, 240 the rotor is rotatably driven by input 250. The generators 220, 230, 240 rotate about axis 260 in rotational direction 265. Stator 227 is fixably coupled to the high shear device wall 255.

The generators include gaps between the rotor and the stator. The first generator 220 comprises a first gap 225; the second generator 230 comprises a second gap 235; and the third generator 240 comprises a third gap 245. The gaps 225, 235, 245 are between about 0.025 mm (0.01 in) and 10.0 mm (0.4 in) wide. Alternatively, the process comprises utilization of a high shear device 200 wherein the gaps 225, 235, 245 are between about 0.5 mm (0.02 in) and about 2.5 mm (0.1 in). In certain instances the gap is maintained at about 1.5 mm (0.06 in). Alternatively, the gaps 225, 235, 245 are different between generators 220, 230, 240. In certain instances, the gap 225 for the first generator 220 is greater than about the gap 235 for the second generator 230, which is greater than about the gap 245 for the third generator 240.

Additionally, the width of the gaps 225, 235, 245 may comprise a coarse, medium, fine, and super-fine characterization. Rotors 222, 223, and 224 and stators 227, 228, and 229 may be toothed designs. Each generator may comprise two or more sets of rotor-stator teeth, as known in the art. Rotors 222, 223, and 224 may comprise a number of rotor teeth circumferentially spaced about the circumference of each rotor. Stators 227, 228, and 229 may comprise a number of stator teeth circumferentially spaced about the circumference of each stator. The rotor and the stator may be of any suitable size. In one embodiment, the inner diameter of the rotor is about 64 mm and the outer diameter of the stator is about 60 mm. In other embodiments, the inner diameter of the rotor is about 11.8 cm and the outer diameter of the stator is about 15.4 cm. In further embodiments, the rotor and stator may have alternate diameters in order to alter the tip speed and shear pressures. In certain embodiments, each of three stages is operated with a super-fine generator, comprising a gap of between about 0.025 mm and about 3 mm. When a feed stream 205 including solid particles is to be sent through high shear device 200, the appropriate gap width is first selected for an appropriate reduction in particle size and increase in particle surface area. In embodiments, this is beneficial for increasing catalyst surface area by shearing and dispersing the particles.

High shear device 200 is fed a reaction mixture comprising the feed stream 205. Feed stream 205 comprises an emulsion of the dispersible phase and the continuous phase. Emulsion refers to a liquefied mixture that contains two distinguishable substances (or phases) that will not readily mix and dissolve together. Most emulsions have a continuous phase (or matrix), which holds therein discontinuous droplets, bubbles, and/or particles of the other phase or substance. Emulsions may be highly viscous, such as slurries or pastes, or may be foams, with tiny gas bubbles suspended in a liquid. As used herein, the term "emulsion" encompasses continuous phases comprising gas bubbles, continuous phases comprising particles (e.g., solid catalyst), continuous phases comprising droplets of a fluid that is substantially insoluble in the continuous phase, and combinations thereof.

Feed stream 205 may include a particulate solid catalyst component. Feed stream 205 is pumped through the generators 220, 230, 240, such that product dispersion 210 is formed. In each generator, the rotors 222, 223, 224 rotate at high speed relative to the fixed stators 227, 228, 229. The rotation of the rotors pumps fluid, such as the feed stream 205, between the outer surface of the rotor 222 and the inner surface of the stator 227 creating a localized high shear condition. The gaps 225, 235, 245 generate high shear forces that process the feed stream 205. The high shear forces between the rotor and stator functions to process the feed stream 205 to create the product dispersion 210. Each generator 220, 230, 240 of the high shear device 200 has interchangeable rotor-stator combinations for producing a narrow distribution of the desired bubble size, if feedstream 205 comprises a gas, or globule size, if feedstream 205 comprises a liquid, in the product dispersion 210.

The product dispersion 210 of gas particles, or bubbles, in a liquid comprises an emulsion. In embodiments, the product dispersion 210 may comprise a dispersion of a previously immiscible or insoluble gas, liquid or solid into the continuous phase. The product dispersion 210 has an average gas particle, or bubble, size less than about 1.5 µm; preferably the bubbles are sub-micron in diameter. In certain instances, the average bubble size is in the range from about 1.0 µm to about 0.1 µm. Alternatively, the average bubble size is less than about 400 nm (0.4 µm) and most preferably less than about 100 nm (0.1 µm).

The high shear device 200 produces a gas emulsion capable of remaining dispersed at atmospheric pressure for at least about 15 minutes. For the purpose of this disclosure, an emulsion of gas particles, or bubbles, in the dispersed phase in product dispersion 210 that are less than 1.5 µm in diameter may comprise a micro-foam. Not to be limited by a specific theory, it is known in emulsion chemistry that sub-micron particles, or bubbles, dispersed in a liquid undergo movement primarily through Brownian motion effects. The bubbles in the emulsion of product dispersion 210 created by the high shear device 200 may have greater mobility through boundary layers of solid catalyst particles, thereby facilitating and accelerating the catalytic reaction through enhanced transport of reactants.

The rotor is set to rotate at a speed commensurate with the diameter of the rotor and the desired tip speed as described hereinabove. Transport resistance is reduced by incorporation of high shear device 200 such that the velocity of the reaction is increased by at least about 5%. Alternatively, the high shear device 200 comprises a high shear colloid mill that serves as an accelerated rate reactor (ARR). The accelerated rate reactor comprises a single stage dispersing chamber. The accelerated rate reactor comprises a multiple stage inline disperser comprising at least 2 stages.

Selection of the high shear device 200 is dependent on throughput requirements and desired particle or bubble size in the outlet dispersion 210. In certain instances, high shear device 200 comprises a Dispax Reactor® of IKA® Works, Inc., Wilmington, N.C. and APV North America, Inc., Wilmington, Mass. Model DR 2000/4, for example, comprises a belt drive, 4M generator, PTFE sealing ring, inlet flange 1" sanitary clamp, outlet flange ¾" sanitary clamp, 2 HP power, output speed of 7900 rpm, flow capacity (water) approximately 300 l/h to approximately 700 l/h (depending on generator), a tip speed of from 9.4 m/s to about 41 m/s (about 1850 ft/min to about 8070 ft/min). Several alternative models are available having various inlet/outlet connections, horsepower, nominal tip speeds, output rpm, and nominal flow rate.

Without wishing to be limited to a particular theory, it is believed that the level or degree of high shear is sufficient to increase rates of mass transfer and may also produce localized non-ideal conditions that enable reactions to occur that would not otherwise be expected to occur based on Gibbs free energy predictions. Localized non ideal conditions are believed to occur within the high shear device resulting in increased temperatures and pressures with the most significant increase believed to be in localized pressures. The increase in pressures and temperatures within the high shear device are instantaneous and localized and quickly revert back to bulk or average system conditions once exiting the high shear device. In some cases, the high shear device induces cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid micro-circulation (acoustic streaming).

Vessel

Vessel or reactor 110 is any type of vessel in which a multiphase reaction can be propagated to carry out the above-described conversion reaction(s). For instance, a continuous or semi-continuous stirred tank reactor, or one or more batch reactors may be employed in series or in parallel. In some applications vessel 110 may be a tower reactor, and in others a tubular reactor or multi-tubular reactor. A catalyst inlet line 115 may be connected to vessel 110 for receiving a catalyst solution or slurry during operation of the system.

Vessel 110 may include one or more of the following components: stirring system, heating and/or cooling capabilities, pressure measurement instrumentation, temperature measurement instrumentation, one or more injection points, and level regulator (not shown), as are known in the art of reaction vessel design. For example, a stirring system may include a motor driven mixer. A heating and/or cooling apparatus may comprise, for example, a heat exchanger. Alternatively, as much of the conversion reaction may occur within HSD 140 in some embodiments, vessel 110 may serve primarily as a storage vessel in some cases. Although generally less desired, in some applications vessel 110 may be omitted, particularly if multiple high shears/reactors are employed in series, as further described below.

Heat Transfer Devices

In addition to the above-mentioned heating/cooling capabilities of vessel 110, other external or internal heat transfer devices for heating or cooling a process stream are also contemplated in variations of the embodiments illustrated in FIG. 1. Some suitable locations for one or more such heat transfer devices are between pump 105 and HSD 140, between HSD 140 and vessel 110, and between vessel 110 and pump 105 when system 1 is operated in multi-pass mode. Some non-limiting examples of such heat transfer devices are shell, tube, plate, and coil heat exchangers, as are known in the art.

Pumps

Pump 105 is configured for either continuous or semi-continuous operation, and may be any suitable pumping device that is capable of providing greater than 2 atm pressure, preferably greater than 3 atm pressure, to allow controlled flow through HSD 140 and system 1. For example, a Roper Type 1 gear pump, Roper Pump Company (Commerce, Ga.) Dayton Pressure Booster Pump Model 2P372E, Dayton Electric Co. (Niles, Ill.) is one suitable pump. Preferably, all contact parts of the pump comprise stainless steel. In some embodiments of the system, pump 105 is capable of pressures greater than about 20 atm. In addition to pump 105, one or more additional, high pressure pump (not shown) may be included in the system illustrated in FIG. 1. For example, a booster pump, which may be similar to pump 105, may be included between HSD 140 and vessel 110 for boosting the pressure into vessel 110. As another example, a supplemental feed pump, which may be similar to pump 105, may be included for introducing additional reactants or catalyst into vessel 110.

Hydration of Alkylene Oxides

In operation for the catalytic hydration of alkylene oxides, respectively, a dispersible alkylene oxide gas stream is introduced into system 100 via line 122, and combined in line 113 with a water stream to form a gas-liquid stream. Alternatively, the alkylene oxide gas may be fed directly into HSD 140, instead of being combined with the liquid reactant (i.e., water) in line 113. Pump 105 is operated to pump the liquid reactant (water) through line 121, and to build pressure and feed HSD 140, providing a controlled flow throughout high shear (HSD) 140 and high shear system 100.

In a preferred embodiment, alkylene oxide gas may be continuously be fed into the water stream 112 to form high shear feed stream 113 (e.g. a gas-liquid stream). In high shear device 140, water and the alkylene oxide vapor are highly dispersed such that nanobubbles and/or microbubbles of alkylene oxide are formed for superior dissolution of alkylene oxide vapor into solution. Once dispersed, the dispersion may exit high shear device 140 at high shear outlet line 118. Stream 118 may optionally enter fluidized or fixed bed 142 in lieu of a slurry catalyst process. However, in a slurry catalyst embodiment, high shear outlet stream 118 may directly enter hydration reactor 110 for hydration. The reaction stream may be maintained at the specified reaction temperature, using cooling coils in the reactor 110 to maintain reaction temperature. Hydration products (e.g. alkylene glycols) may be withdrawn at product stream 116.

Figure 2:
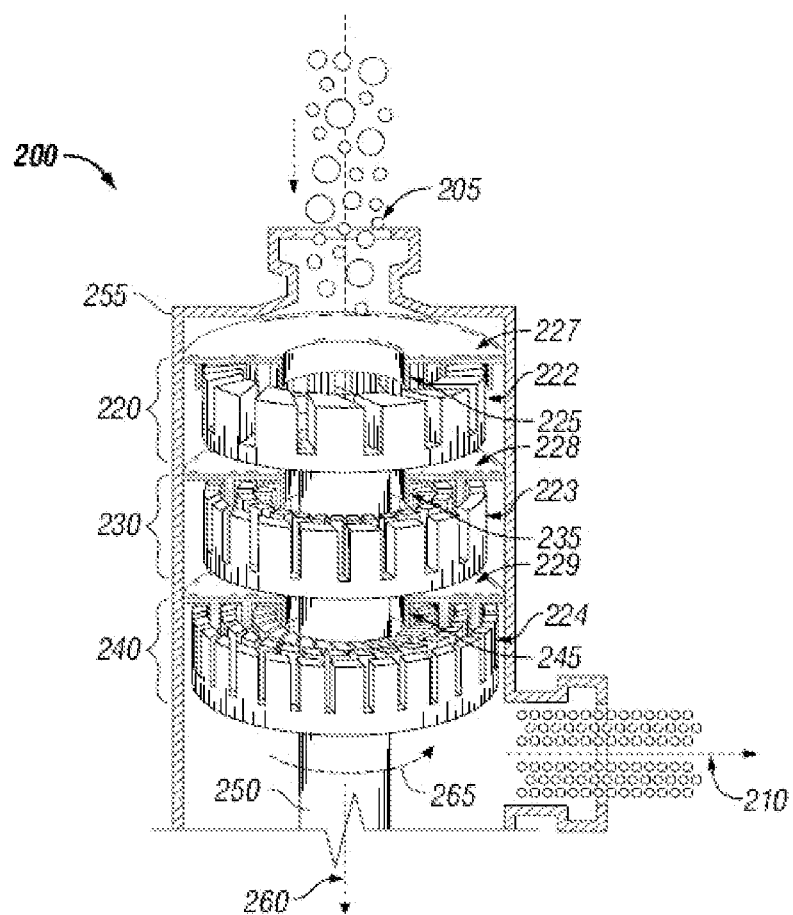
FIG. 2 is a longitudinal cross-section view of a multi-stage high shear device, as employed in an embodiment of the system of FIG. 1.

In an exemplary embodiment, the high shear device comprises a commercial disperser such as IKA® model DR 2000/4, a high shear, three stage dispersing device configured with three rotors in combination with stators, aligned in series. The disperser is used to create the dispersion of alkylene oxides in the liquid medium comprising water (i.e., "the reactants"). The rotor/stator sets may be configured as illustrated in FIG. 2, for example. The combined reactants enter the high shear device via line 113 and enter a first stage rotor/stator combination having circumferentially spaced first stage shear openings. The coarse dispersion exiting the first stage enters the second rotor/stator stage, which has second stage shear openings. The reduced bubble-size dispersion emerging from the second stage enters the third stage rotor/stator combination having third stage shear openings. The dispersion exits the high shear device via line 118. In some embodiments, the shear rate increases stepwise longitudinally along the direction of the flow. For example, in some embodiments, the shear rate in the first rotor/stator stage is greater than the shear rate in subsequent stage(s). In other embodiments, the shear rate is substantially constant along the direction of the flow, with the stage or stages being the same. If the high shear device includes a PTFE seal, for example, the seal may be cooled using any suitable technique that is known in the art. For example, the reactant stream flowing in line 113 may be used to cool the seal and in so doing be preheated as desired prior to entering the high shear device.

The rotor of HSD 140 is set to rotate at a speed commensurate with the diameter of the rotor and the desired tip speed. As described above, the high shear device (e.g., colloid mill) has either a fixed clearance between the stator and rotor or has adjustable clearance. HSD 140 serves to intimately mix the alkylene oxide vapor and the reactant liquid (i.e., water). In some embodiments of the process, the transport resistance of the reactants is reduced by operation of the high shear device such that the velocity of the reaction (i.e. reaction rate) is increased by greater than a factor of about 5. In some embodiments, the velocity of the reaction is increased by at least a factor of 10. In some embodiments, the velocity is increased by a factor in the range of about 10 to about 100 fold. In some embodiments, HSD 140 delivers at least 300 L/h with a power consumption of 1.5 kW at a nominal tip speed of at least 4500 ft/min, and which may exceed 7900 ft/min (140 m/sec). Although measurement of instantaneous temperature and pressure at the tip of a rotating shear unit or revolving element in HSD 140 is difficult, it is estimated that the localized temperature seen by the intimately mixed reactants may be in excess of 500° C. and at pressures in excess of 500 kg/cm$^2$ under high shear conditions. The high shear results in dispersion of the alkylene oxide gas in micron or submicron-sized bubbles. In some embodiments, the resultant dispersion has an average bubble size less than about 1.5 μm. Accordingly, the dispersion exiting HSD 140 via line 118 comprises micron and/or submicron-sized gas bubbles. In some embodiments, the mean bubble size is in the range of about 0.4 μm to about 1.5 μm. In some embodiments, the mean bubble size is less than about 400 nm, and may be about 100 nm in some cases. In many embodiments, the microbubble dispersion is able to remain dispersed at atmospheric pressure for at least 15 minutes.

Once dispersed, the resulting alkylene oxide/water dispersion exits HSD 140 via line 118 and feeds into vessel 110, as illustrated in FIG. 1. As a result of the intimate mixing of the reactants prior to entering vessel 110, a significant portion of the chemical reaction may take place in HSD 140, with or without the presence of a catalyst. Accordingly, in some embodiments, reactor/vessel 110 may be used primarily for heating and separation of volatile reaction products from the alkylene glycol product. Alternatively, or additionally, vessel 110 may serve as a primary reaction vessel where most of the alkylene glycol product is produced. Vessel/reactor 110 may be operated in either continuous or semi-continuous flow mode, or it may be operated in batch mode. The contents of vessel 110 may be maintained at a specified reaction temperature using heating and/or cooling capabilities (e.g., cooling coils) and temperature measurement instrumentation. Pressure in the vessel may be monitored using suitable pressure measurement instrumentation, and the level of reactants in the vessel may be controlled using a level regulator (not shown), employing techniques that are known to those of skill in the art. The contents are stirred continuously or semi-continuously.

Commonly known hydration reaction conditions may suitably be employed as the conditions of the production of an alkylene glycol by hydrating alkylene oxides by using catalysts. There is no particular restriction as to the reaction conditions. For exemplary purposes, the method will be discussed with respect to ethylene glycol. However, it is envisioned that embodiments of the method may be used to produce any alkylene glycol. In the production of ethylene glycol, theoretically one mole of water is required to hydrate one mole of ethylene oxide. Actually, however, greater than equal molecular proportions of water to ethylene oxide are required for good results. Although a conversion of approximately 90% can sometimes be obtained when employing a reactant ratio of water to ethylene oxide of around 2, reactant ratios of greater than 6 are generally required to achieve reasonably high yields of products, otherwise the ethylene glycol formed reacts with ethylene oxide to form di- and triethylene glycols. The effects of the reactant ratios on the results obtained for the production of ethylene glycol and other alkylene glycols are well known. In reacting steam and ethylene oxide in a ratio of at least 17:1 over a stationary bed of the claimed catalyst, yields based on the ethylene oxide consumed are found to be reasonably high.

The primary by-products of the hydrolysis reaction are di- and polyglycols, e.g., dialkylene glycol, trialkylene glycol and tetra-alkylene glycol. The formation of the di- and polyglycols is believed to be primarily due to the reaction of alkylene oxide with alkylene glycol. As alkylene oxides are generally more reactive with alkylene glycols than they are with water, large excesses of water are employed in order to favor the reaction with water and thereby obtain a commercially-attractive selectivity to the monoglycol product.

The reaction temperature, which varies depending upon the type of the starting alkylene oxide, the type of the catalyst, the composition of the reactant mixture at the early stage of the reaction, etc., is generally 50° C. to 200° C., preferably 110° C. to 160° C. The reaction pressure, which varies according to reaction temperature, and the extent of advance of the reaction, is generally 3 to 50 kg/cm$^2$. If desired, the pressure within the reactor may be adjusted occasionally. The reaction time may be about 30 minutes to about 3 hours. The contacting time of the reactants over a catalyst can vary anywhere from period of less than a second to periods ranging up to 25 seconds.

The alkylene oxides for the reaction may be used alone or in combination as a mixture of different types. The alkylene oxides can have any structure, such as, aliphatic, aromatic, heteroaromatic, aliphatic-aromatic or aliphatic-heteroaromatic. They can also contain other functional groups, and it should be determined beforehand whether these functional groups should remain unchanged or should be hydrated themselves.

Embodiments of the disclosed process may be suitable for hydrating straight or branched alkylene oxides. Example of alkylene oxides include without limitation, ethylene oxide, butylenes oxide, propylene oxide, and the like. The alkylene oxide may have from 2 to 4 carbon atoms.

In an embodiment, liquid alkylene oxide is used as feed in the hydration reaction. For example, ethylene oxide (EO) is introduced into the HSD unit as a liquid. Due to the cavitation conditions created by high shear, alkylene oxide may form small gas bubbles (diameter less than 1 micron) dispersed in the liquid phase or alkylene oxide may remain liquid and become intimately mixed with water for the hydration reaction to produce alkylene glycol.

In some embodiments, the hydration reaction takes place in the HSD as a thermal conversion reactor. A thermal conversion reactor is a reactor wherein the reaction may be promoted by heat alone and does not require or contain a catalyst. After the alkylene oxide is converted to its corresponding alkylene glycol, the effluent from the HSD is sent to a distillation column to separate the alkylene glycol from unreacted reactants (e.g., excess water). The reaction conditions in the HSD (acting as a thermal conversion reactor) are generally in accordance with those commonly used in thermal alkylene glycol production except that the HSD is able to produce high temperature and high pressure in a localized manner due to the cavitation effect. Therefore the global temperature and pressure may not need to be as severe as required by the hydration reactions. The reaction conditions listed below as examples are considered to be localized reaction conditions in the HSD. The water to alkylene oxide ratio is in the range of from 15 to 30 moles of water per mole of alkylene oxide. The reaction temperature is in the range of from 150° C. to 250° C. The reaction pressure is in the range of from 500 to 5000 kPa.

In some other embodiments, the hydration reaction takes place in a vessel that receives the effluent of the HSD, wherein said vessel contains a suitable catalyst for the hydration reactions of alkylene oxides. Such a vessel serves as a catalytic conversion reactor. A catalytic conversion reactor is a reactor comprising a catalyst capable of promoting the conversion of alkylene oxide to alkylene glycol(s). The catalytic conversion reaction may be conducted in the presence of carbon dioxide. Whether to provide carbon dioxide to the reaction may depend on whether a catalyst is utilized in the reactor and the type of catalyst used. For example, if an anion exchange resin is utilized as a catalyst it may be desirable to provide an amount of carbon dioxide to the catalyst bed. The carbon dioxide may be provided to the catalytic conversion reactor in any convenient manner. The carbon dioxide may, for instance, be introduced separately and/or with one or more of the feed streams. Carbon dioxide may be present in the reaction mixture in gaseous form or in the form of carbonic acid or in the form of salts of carbonic acid. In some cases, carbon dioxide is present in the reaction mixture in an amount no greater than 0.1 wt %; in some other cases, carbon dioxide is present in the reaction mixture in an amount no greater than 0.05 wt %; in yet other cases, carbon dioxide is present in the reaction mixture in an amount no greater than 0.01 wt %, based on the total amount of reactants in the catalytic conversion reactor.

In some further embodiments, the thermal and catalytic conversion reactors are positioned in a series configuration. For example, as shown in FIG. 1, HSD 140 acts as a thermal conversion reactor and vessel 110 serves as a catalytic conversion reactor for the hydration of alkylene oxides. The effluent 118 from HSD 140 may contain some unreacted reactants (e.g., an alkylene oxide and water) and such residue reactants may be reacted in the catalytic conversion reactor 110 to continue to produce alkylene glycol(s). Additional reactants (e.g., alkylene oxide or water or both) and additives (e.g., carbon dioxide) may be added to vessel 110 via any means known to one skilled in the art (not shown in FIG. 1). Effluent 116 from vessel 110 contains alkylene glycol(s), water, and maybe some unreacted alkylene oxide. In some cases, effluent 116 is sent to a distillation column to recover the alkylene glycol(s). In some other cases, effluent 116 is recycled to the HSD 140 for further reaction.

In some further embodiments, the thermal and catalytic conversion reactors are positioned in a parallel configuration (not shown). In other embodiments, the thermal and catalytic conversion reactors are positioned in a combined series and parallel configuration. The catalytic conversion reactor is generally downstream of the thermal conversion reactor in a series configuration. One of ordinary skill in the art with the aid of this disclosure is able to design various configurations of the thermal and catalytic conversion reactors for the hydration reaction of alkylene oxides; therefore all such configurations are within the scope of this disclosure.

In some further embodiments, catalyst slurry is introduced into the HSD together with an alkylene oxide and water so that the HSD serves as a catalytic conversion reactor facilitated by cavitation effect. In yet some other embodiments, the HSD comprises a catalytic surface and therefore functions as a catalytic conversion reactor facilitated by the cavitation effect. The localized high temperature and high pressure in the HSD cause the catalytic conversion reaction (from alkylene oxide to alkylene glycol) to take place under mild global temperature and pressure conditions. In some cases, the reaction rate and selectivity are improved. In some cases, the molar ratio of water to alkylene oxide is reduced so that the recovery of alkylene glycol is made easier. In some embodiments, sintered metals, (e.g., INCONEL® alloys, HASTELLOY® materials) are be used to construct at least one surface of the HSD. For example, the rotors, stators, and/or other components of the HSD may be manufactured of refractory materials (e.g. sintered metal). In certain embodiments, the rotor and the stator comprise no teeth, thus forcing the reactants to flow through pores, for example, of a sintered material.

Catalyst

If a catalyst is used to promote the hydration reaction, it may be introduced into the vessel via line 115, as an aqueous or nonaqueous slurry or stream. Alternatively, or additionally, catalyst may be added elsewhere in the system 100. For example, catalyst slurry may be injected into line 121. In some embodiments, line 121 may contain a flowing water stream and/or alkylene oxide recycle stream from vessel 110.

In embodiments, any catalyst suitable for catalyzing a hydration reaction may be employed. An inert gas such as nitrogen may be used to fill reactor 110 and purge it of any air and/or oxygen. According to one embodiment, the catalysts useful in the disclosed process may be acid catalysts. For example, partially amine-neutralized sulfonic acid catalysts may be used as the catalyst. These catalysts are heterogeneous and may be described more completely as sulfonic acid-type ion exchange resins. These resins are then modified by passing sufficient amine through the resin to partially neutralize the sulfonic acid groups contained therein. Primary, secondary or tertiary amines are each acceptable. Tertiary amines may be used in the disclosed process. The result is a catalyst which consists of a mixture of the original free sulfonic acid and the amine salt of the sulfonic acid, all still in the heterogeneous form.

In a specific embodiment, catalyst comprises a styrene-divinylbenzene copolymer matrix with pendant sulfonic acid groups. Catalysts falling within this species are available from Rohm and Haas under the designation Amberlyst™ RTM 15 and Amberlyst™ XN-1010 which differ in the amount of surface area available. Other matrices than the styrene-divinylbenzene type could be used, including other organic polymers and inorganic materials, provided only that the substrate be capable of binding the sulfonic acid groups to maintain a heterogeneous catalyst system.

Other representatives of the numerous acid catalysts that have been suggested for use in the hydration of alkylene oxides include fluorinated alkyl sulfonic acid ion exchange resins, carboxylic acids and halogen acids, strong acid cation exchange resins, aliphatic mono- and/or polycarboxylic acids, cationic exchange resins, acidic zeolites, sulfur dioxide, trihalogen acetic acids.

In addition to the acid catalysts, numerous catalysts have been suggested for the hydration of alkylene oxides. For example, the catalyst may be an aluminum phosphate catalyst, organic tertiary amines such as triethylamine and pyridine, quarternary phosphonium salts, fluoroalkyl sulfonic acid resins, alkali metal halides such as chlorides, bromides and iodides of potassium, sodium and lithium, or quaternary ammonium halides such as tetramethylammonium iodide and tetraethylammonium bromide, or combinations thereof.

Various metal-containing compounds, including metal oxides, may be used as catalysts for the hydrolysis of alkylene oxides. For example, a dehydrating metal oxide such as without limitation, alumina, thoria, or oxides or tungsten, titanium, vanadium, molybdenum or zirconium. Or alternatively alkali metal bases may be used such as alcoholates, oxides of titanium, tungsten and thorium.

The catalyst may also comprise an organometallic compounds including metals such as vanadium, molybdenum, tungsten, titantium, chromium, zirconium, selenium, tellurium, tantalum, rhenium, uranium, or combinations thereof.

More recently, U.S. Pat. No. 4,277,632, issued Jul. 7, 1981, discloses a process for the production of alkylene glycols by the hydrolysis of alkylene oxides in the presence of a catalyst of at least one member selected from the group consisting of molybdenum and tungsten. Catalyst may be fed into reactor 110 through catalyst feed stream 115. Alternatively, catalyst may be present in a fixed or fluidized bed 142.

The bulk or global operating temperature of the reactants is desirably maintained below their flash points. In some embodiments, the operating conditions of system 100 comprise a temperature in the range of from about 50° C. to about 300° C. In specific embodiments, the reaction temperature in vessel 110, in particular, is in the range of from about 90° C. to about 220° C. In some embodiments, the reaction pressure in vessel 110 is in the range of from about 5 atm to about 50 atm.

The dispersion may be further processed prior to entering vessel 110 (as indicated by arrow 18), if desired. In vessel 110, alkylene oxide hydration occurs via catalytic hydration. The contents of the vessel are stirred continuously or semi-continuously, the temperature of the reactants is controlled (e.g., using a heat exchanger), and the fluid level inside vessel 110 is regulated using standard techniques. Alkylene oxide hydration may occur either continuously, semi-continuously or batch wise, as desired for a particular application. Any reaction gas that is produced exits reactor 110 via gas line 117. This gas stream may comprise unreacted alkylene oxides, for example. The reaction gas removed via line 117 may be further treated, and the components may be recycled, as desired.

The reaction product stream including unconverted alkylene oxides and corresponding byproducts exits (e.g. di- and polyglycols, dialkylene glycol, trialkylene glycol and tetraalkylene glycol) vessel 110 by way of line 116. The alkylene glycol product may be recovered and treated as known to those of skill in the art.

Production of Polyethylene Glycol (PEG)

In some embodiments, hydration of ethylene oxides leads to the production of polyethylene glycols (PEG's). In an embodiment, PEG's are produced by reacting ethylene oxide with water. In another embodiment, PEG's are produced by reacting ethylene oxide with ethylene glycol. In yet another embodiment, PEG's are produced by reacting ethylene oxide with ethylene glycol oligomers. In some embodiments, ethylene glycol or ethylene glycol oligomers are used as a starting material instead of water, because it allows the production PEG's with a low polydispersity. Such reactions are catalyzed by acidic or basic catalysts, such as magnesium-, aluminium- or calcium-organoelement compounds, and alkali catalysts (sodium hydroxide, potassium hydroxide, or sodium carbonate).

In an embodiment, feed streams of ethylene oxide and water or ethylene glycol or ethylene glycol oligomers are intimately mixed in HSD 140 (FIG. 1). Effluent 118 from HSD 140 is introduced into a fixed or fluidized bed 142 comprising a catalyst that promotes the formation of PEG. In some cases, catalyst slurry is used and such slurry is introduced into vessel 110 via line 115 together with effluent 119 from bed reactor 142. In some other cases, bed reactor 142 is omitted and catalyst slurry and effluent 118 from HSD 140 are introduced into vessel/reactor 110. The production of PEG takes place under the action of suitable catalysts. Due to the exothermic nature of the reaction, cooling systems are provided for bed reactor 142 and/or vessel 110 to prevent runaway polymerization reactions. In some embodiments, the produced PEG is recovered from effluent 116 from vessel 110. In some embodiments, effluent 116 from vessel 110 is recycled to HSD 140 for further processing.

In an embodiment, feed streams of ethylene oxide and water (or ethylene glycol or ethylene glycol oligomers) are introduced into HSD, wherein said HSD comprises a catalytic surface that promotes the formation of PEG's. In another embodiment, catalyst slurry and feed streams of ethylene oxide and water (or ethylene glycol or ethylene glycol oligomers) are introduced into HSD. The production of PEG's takes place in HSD under the action of the catalyst. In some cases, a cooling system is provided to HSD to prevent runaway polymerization reactions. In some embodiments, the effluent from HSD is recycled as feed to HSD for further processing. In some other cases, the effluent from HSD is introduced into a second HSD to further produce PEG's.

Multiple Pass Operation

In the embodiment shown in FIG. 1, the system is configured for single pass operation, wherein the output from vessel 110 goes directly to further processing for recovery of alkylene glycol product. In some embodiments it may be desirable to pass the contents of vessel 110, or a liquid fraction containing unreacted alkylene oxide, through HSD 140 during a second pass. In this case, line 116 is connected to line 121 via dotted line 120, and the recycle stream from vessel 110 is pumped by pump 105 into line 113 and thence into HSD 140. Additional alkylene oxide gas may be injected via line 122 into line 113, or it may be added directly into the high shear device (not shown).

Multiple High Shear Devices

In some embodiments, two or more high shear devices like HSD 140, or configured differently, are aligned in series, and are used to further enhance the reaction. Their operation may be in either batch or continuous mode. In some instances in which a single pass or "once through" process is desired, the use of multiple high shear devices in series may also be advantageous. In some embodiments where multiple high shear devices are operated in series, vessel 110 may be omitted. In some embodiments, multiple high shear devices 140 are operated in parallel, and the outlet dispersions therefrom are introduced into one or more vessel 110.

While embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations. Use of broader terms such as comprises, includes, having, etc. should be understood to provide support for narrower terms such as consisting of, consisting essentially of, comprised substantially of, and the like. Accordingly, the scope of protection is not limited by the description set out above but is only limited by the claims which follow, that scope including all equivalents of the subject matter of the claims. Each and every original claim is incorporated into the specification as an embodiment of the invention. Thus, the claims are a further description and are an addition to the preferred embodiments of the present invention. The disclosures of all patents, patent applications, and publications cited herein are hereby incorporated by reference, to the extent they provide exemplary, procedural or other details supplementary to those set forth herein.

What is claimed is:

1. A method of hydrating an alkylene oxide comprising:
   introducing an alkylene oxide into water to form a first stream;
   flowing the first stream through a high shear device to produce a second stream; and
   contacting the second stream with a catalyst in a reactor to hydrate the alkylene oxide and form an alkylene glycol.

2. The method of claim 1, wherein the alkylene oxide is selected from the group consisting of ethylene oxide, propylene oxide, butylene oxide, and combinations thereof.

3. The method of claim 1, the method further comprising operating the high shear device at a tip speed of at least about 23 m/sec.

4. The method of claim 1, the method further comprising operating the high shear device at a shear rate of greater than about $20,000 \text{ s}^{-1}$.

5. The method of claim 1, wherein producing the second stream comprises an energy expenditure by the high shear device of at least about $1000 \text{ W/m}^3$.

6. The method of claim 1, wherein the catalyst is selected from the group consisting of an amine, an acid catalyst, an organometallic compound, an alkali metal halide, a quaternary ammonium halide, zeolites, and combinations thereof.

7. The method of claim 1, wherein the alkylene glycol comprises ethylene glycol.

8. A method of hydrating an alkylene oxide comprising:
   introducing an alkylene oxide into water to form a first stream;
   flowing the first stream through a high shear device to produce a second stream comprising high shear treated alkylene oxide; and
   contacting the second stream with a catalyst in a reactor to hydrate at least a portion of the high shear treated alkylene oxide.

9. The method of claim 8, wherein by way of contact with the catalyst the portion of the high shear treated alkylene oxide forms alkylene.

10. The method of claim 8, wherein in the reactor the alkylene oxide is hydrated to form ethylene glycol.

11. The method of claim 8, wherein the reactor is a fixed bed reactor, and wherein the catalyst is a hydration catalyst.

12. The method of claim 8, the method further comprising operating the high shear device at a shear rate in the range of about $20,000 \text{ s}^{-1}$ to about $1,600,000 \text{ s}^{-1}$.

13. A method of producing polyethylene glycol comprising:
   introducing a first component comprising ethylene oxide and a second component selected from the group consisting of water, ethylene glycol, and ethylene glycol oligomer, into a high shear device to produce a first stream; and
   reacting at least a portion of the first stream with a catalyst to produce polyethylene glycol.

14. The method of claim 13, wherein the high shear device comprises a catalytic surface that promotes formation of polyethylene glycol.

15. The method of claim 13, wherein the reacting step occurs in a fixed bed reactor.

16. The method of claim 13, the method further comprising operating the high shear device at a shear rate in the range of about $20,000 \text{ s}^{-1}$ to about $1,600,000 \text{ s}^{-1}$.

17. The method of claim 16, wherein the high shear device comprises a catalytic surface.

* * * * *